(12) United States Patent
Roos et al.

(10) Patent No.: US 9,114,433 B2
(45) Date of Patent: Aug. 25, 2015

(54) MULTI-FRACTIONAL COAL SORTER AND METHOD OF USE THEREOF

(71) Applicant: Mineral Separation Technologies, Inc., Coal Center, PA (US)

(72) Inventors: Charles E. Roos, Nashville, TN (US); Edward J. Sommer, Jr., Nashville, TN (US); Charles D. Roos, New York, NY (US)

(73) Assignee: Mineral Separation Technologies, Inc., Coal Center, PA (US)

( * ) Notice: Subject to any disclaimer, the term of this patent is extended or adjusted under 35 U.S.C. 154(b) by 0 days.

(21) Appl. No.: 13/742,228

(22) Filed: Jan. 15, 2013

(65) Prior Publication Data

US 2013/0184853 A1      Jul. 18, 2013

Related U.S. Application Data

(60) Provisional application No. 61/632,016, filed on Jan. 17, 2012.

(51) Int. Cl.
| | |
|---|---|
| *B07C 5/346* | (2006.01) |
| *B07C 5/12* | (2006.01) |
| *H01J 35/02* | (2006.01) |
| *G01N 23/06* | (2006.01) |
| *G01N 23/083* | (2006.01) |

(Continued)

(52) U.S. Cl.
CPC . *B07C 5/12* (2013.01); *B07C 5/346* (2013.01); *B07C 5/363* (2013.01); *G01N 23/02* (2013.01); *G01N 23/06* (2013.01); *G01N 23/083* (2013.01); *G01N 23/12* (2013.01); *H01J 35/02* (2013.01); *G21K 1/02* (2013.01); *Y10T 29/49826* (2013.01)

(58) Field of Classification Search
CPC .... B07C 12/12; B07C 12/363; B07C 12/342; G01N 23/02; G01N 23/12; G01N 23/083
USPC ......... 209/589, 576; 378/51, 54, 69, 145, 147
See application file for complete search history.

(56) References Cited

U.S. PATENT DOCUMENTS 2,679,317 A * 5/1954 Roop ........................... 209/560
3,270,204 A     8/1966 Rhodes (Continued)

FOREIGN PATENT DOCUMENTS

| CN | 1125645 A | 7/1996 |
|---|---|---|
| CN | 101214483 A | 7/2008 |

(Continued)

OTHER PUBLICATIONS

"Suffer dioxide and coal" (author unknown), http://www.sourcewatch.org/index.php/Sulfur_dioxide_and_coal, SourceWatch, pp. 1-6, Feb. 8, 2010.

(Continued)

*Primary Examiner* — Ernesto Suarez
(74) *Attorney, Agent, or Firm* — Frost Brown Todd LLC

(57) ABSTRACT

Disclosed herein are methods of sorting coal into multiple fractions based upon x-ray absorption and size characteristics in order to remove rocks and other contaminants of various sizes from coal. The use of such dry processing of coal is desirable as it reduces pollution and transportation costs. The multi-fractional sorting of coal is a more efficient manner for identifying and removing rock and contaminants from coal.

3 Claims, 13 Drawing Sheets

(51) Int. Cl.
*G01N 23/02* (2006.01)
*G01N 23/12* (2006.01)
*B07C 5/36* (2006.01)
*G21K 1/02* (2006.01)

(56) References Cited

U.S. PATENT DOCUMENTS

| | | | |
|---|---|---|---|
| 3,448,264 A | | 6/1969 | Rhodes |
| 3,472,375 A | * | 10/1969 | Mathews ............... 209/576 |
| 3,655,964 A | * | 4/1972 | Slight .................. 378/53 |
| 4,064,440 A | * | 12/1977 | Roder .................. 378/57 |
| 4,090,074 A | | 5/1978 | Watt et al. |
| 4,377,392 A | | 3/1983 | Massey et al. |
| 4,462,495 A | * | 7/1984 | McKinley et al. ........... 209/33 |
| 4,486,894 A | | 12/1984 | Page et al. |
| 4,549,659 A | * | 10/1985 | Hawkins et al. ........... 209/3.2 |
| 4,566,114 A | | 1/1986 | Watt et al. |
| 4,626,688 A | | 12/1986 | Barnes |
| 4,731,807 A | * | 3/1988 | Plessis et al. ............ 378/156 |
| 4,768,216 A | | 8/1988 | Harvey et al. |
| 4,815,116 A | | 3/1989 | Cho |
| 4,848,590 A | * | 7/1989 | Kelly .................. 209/564 |
| 5,176,260 A | | 1/1993 | Oder |
| 5,339,962 A | | 8/1994 | Sommer, Jr. et al. |
| 5,676,256 A | | 10/1997 | Kumar et al. |
| 5,738,224 A | | 4/1998 | Sommer, Jr. et al. |
| 5,794,788 A | * | 8/1998 | Massen .................. 209/524 |
| 5,818,899 A | | 10/1998 | Connolly et al. |
| 5,841,832 A | | 11/1998 | Mazess et al. |
| 5,841,833 A | | 11/1998 | Mazess et al. |
| 5,854,821 A | | 12/1998 | Chase et al. |
| 5,931,308 A | | 8/1999 | Gesing et al. |
| RE36,537 E | | 2/2000 | Sommer, Jr. et al. |
| 6,122,343 A | | 9/2000 | Pidcock |
| 6,128,365 A | | 10/2000 | Bechwati et al. |
| 6,266,390 B1 | | 7/2001 | Sommer, Jr. et al. |
| 6,272,230 B1 | | 8/2001 | Hiraoglu et al. |
| 6,338,305 B1 | | 1/2002 | McHenry et al. |
| RE37,536 E | | 2/2002 | Barnes |
| 6,364,528 B1 | | 4/2002 | Rossiger |
| 6,370,223 B1 | | 4/2002 | Gleason et al. |
| 6,399,951 B1 | | 6/2002 | Paulus et al. |
| 6,453,003 B1 | * | 9/2002 | Springer et al. ........... 378/57 |
| 6,519,315 B2 | | 2/2003 | Sommer, Jr. et al. |
| 6,545,240 B2 | | 4/2003 | Kimar |
| 6,610,981 B2 | | 8/2003 | Sommer, Jr. |
| 6,661,867 B2 | | 12/2003 | Mario et al. |
| 6,855,901 B1 | | 2/2005 | Guenard et al. |
| 6,888,917 B2 | | 5/2005 | Sommer, Jr. et al. |
| 7,012,256 B1 | | 3/2006 | Roos et al. |
| 7,099,433 B2 | | 8/2006 | Sommer, Jr. et al. |
| 7,200,200 B2 | | 4/2007 | Laurila et al. |
| 7,244,941 B2 | | 7/2007 | Roos et al. |
| 7,286,634 B2 | | 10/2007 | Sommer, Jr. et al. |
| 7,356,115 B2 | | 4/2008 | Ford et al. |
| 7,542,873 B2 | | 6/2009 | Vince et al. |
| 7,558,370 B2 | | 7/2009 | Sommer, Jr. et al. |
| 7,564,943 B2 | | 7/2009 | Sommer, Jr. et al. |
| 7,664,225 B2 | | 2/2010 | Klein |
| 7,848,484 B2 | | 12/2010 | Sommer, Jr. et al. |
| 8,144,831 B2 | | 3/2012 | Sommer, Jr. et al. |
| 8,155,894 B2 | | 4/2012 | Kabumoto |
| 8,422,630 B2 | | 4/2013 | Matoba |
| 8,692,148 B1 | | 4/2014 | Sommer, Jr. et al. |
| 2004/0066890 A1 | | 4/2004 | Dalmijn et al. |
| 2005/0232391 A1 | | 10/2005 | Katz |
| 2010/0185319 A1 | | 7/2010 | Petzold et al. |
| 2010/0219109 A1 | | 9/2010 | Roos et al. |
| 2013/0208856 A1 | * | 8/2013 | Klein .................. 378/53 |

FOREIGN PATENT DOCUMENTS

| | | | |
|---|---|---|---|
| EP | 64810 A1 | * | 11/1982 |
| EP | 0484221 A2 | | 5/1992 |
| EP | 0484221 A3 | | 5/1992 |
| EP | 0942295 A2 | | 9/1999 |
| EP | 0942295 A3 | | 11/2001 |
| GB | 2285506 A | | 7/1995 |
| WO | 0109596 A1 | | 2/2001 |
| WO | WO 2004/106897 | | 12/2004 |

OTHER PUBLICATIONS

"Mercury Emissions from China" (author unknown), http://energy.er.usgs.gov/health_environment/mercury/mercury_china_emissions.html, U.S. Geological Survey, pp. 1-3, Feb. 14, 2010.

"Mercury in Coal" (author unknown), http://energy.er.usgs.gov/health_environment/mercury/mercury_coal.html, U.S. Geological Survey, pp. 1-3, Feb. 14, 2010.

Tako P.R., De Jong et al., "Automatic Sorting and Control in Solid Fuel Processing: Opportunities in European Perspective"; Geologica Belgica; 2004; pp. 325-333; vol. 7/3-4; Geologica Belgica; Brussels, Belgium.

* cited by examiner

| density | 5.0 g/cc | 1.2 g/cc | 2.6 g/cc |
|---|---|---|---|
| Energy (kev) | FeS (Coefficient $\mu$ (cm$^{-1}$)) | Coal (Coefficient $\mu$ (cm$^{-1}$)) | SiO$_2$ (Coefficient $\mu$ (cm$^{-1}$)) |
| 6.00 | 763.20 | 7.730 | 227.10 |
| 8.00 | 963.70 | 3.160 | 99.200 |
| 10.00 | 530.70 | 1.680 | 51.790 |
| 15.00 | 174.17 | 0.570 | 15.830 |
| 20.00 | 77.67 | 0.312 | 6.930 |
| 30.00 | 24.64 | 0.181 | 2.360 |
| 40.00 | 11.06 | 0.147 | 1.250 |
| 50.00 | 6.02 | 0.132 | 0.847 |
| 60.00 | 3.87 | 0.124 | 0.666 |
| 80.00 | 2.08 | 0.114 | 0.547 |
| 100.00 | 1.41 | 0.107 | 0.440 |

Figure 9

MULTI-FRACTIONAL COAL SORTER AND METHOD OF USE THEREOF

This application claims the benefit of U.S. Provisional Patent Application Ser. No. 61/632,016, filed Jan. 17, 2012, entitled "Multi-fractional coal sorter" which is hereby incorporated by reference in its entirety.

Be it known that we, Charles E. Roos, a citizen of the United States, residing at 2507 Ridgewood Drive, Nashville, Tenn. 37215, Edward J. Sommer, Jr., a citizen of the United States, residing at 5329 General Forrest Court, Nashville, TN 37215, and Charles D. Roos, a citizen of the United States, residing at 306 West 100$^{th}$ Street #31, New York, N.Y. 10025, have invented new and useful "Multi-Fractional Coal Sorter and Method of Use Thereof."

BACKGROUND OF THE INVENTION

Run of mine (ROM) coal is used for energy production after it is processed. Wet processing can reduce the ash and sulfur content of the coal, but it wets the processed coal. There are many drawbacks to wet processing. For example, the liquid media requires treatment in a wastewater treatment facility. Coal fines and water produce sludge with environmental problems. Some processes use acids to remove contaminants and pollute water. The latent heat of water in wet coal reduces the recoverable energy from the combustion of coal by one to two percent. This reduction in useful energy increases the carbon footprint to produce electrical power. Some 95% of coal processing currently uses wet methods.

A preferred method for processing ROM coal is dry processing. Generally, ROM coal includes a number of rocks of different sizes and compositions (fractions). Their sizes can range from small pebbles (for example 2 mm) to larger rocks (for example 70 mm and even greater) and their composition variable from silicates to iron pyrites. These rocks have a higher density than the coal. Dry processing does not create ecologically undesirable waste or require complex permits. The coal fines, which can be a substantial proportion of the fuel value in the coal, are not affected by dry processing. A commercially useful coal sorter must provide high throughput while it removes rocks and has minimal loss of fuel value. Accordingly, enhancing currently existing dry processing methods and devices is needed.

SUMMARY OF THE INVENTION

The present invention discloses methods of sorting materials into multiple fractions. Multi-fractional coal sorting devices are also disclosed. The devices and disclosed methods use x-rays for sorting. In certain embodiments, a method of sorting materials into multiple fractions, includes providing a sample, receiving a collimated x-ray beam from an x-ray tube by a detector, determining measurements of x-ray absorption of pieces of the sample, identifying small and large pieces in the sample having a higher density than coal, sorting the large pieces from the sample by use of an air blast, and sorting the small pieces from the sample by use of a smaller air blast. Another embodiment of the invention further includes separating the sorted large pieces from ejected coal by use of a screen. Still another embodiment of the invention further includes separating the sorted small pieces from ejected coal by use of a screen. Another embodiment of the invention includes receiving the collimated x-ray beam by the detector is receiving a plurality of collimated x-ray beams. Yet another embodiment of the invention includes receiving the collimated x-ray beam by the detector which further includes receiving a first collimated x-ray beam from the x-ray tube by a first detector, and receiving a second collimated x-ray beam from the x-ray tube by a second detector. Yet another embodiment of the invention further includes determining identifying characteristics of the sample by use of an infrared 3D imager.

Another embodiment of the invention is a multi-fractional coal sorting device, including an x-ray tube, wherein the x-ray tube is in a fixed position, a first collimator attached to the x-ray tube, a second collimator attached to the x-ray tube, a first x-ray detector, wherein the first x-ray detector is in a fixed position to receive x-rays collimated by the first collimator, a second x-ray detector, wherein the second x-ray detector is in a fixed position to receive x-rays collimated by the second collimator, a first microprocessor operationally connected to the first x-ray detector, a first sized ejector operationally connected to the first microprocessor, a second microprocessor operationally connected to the second x-ray detector, a second sized ejector operationally connected to the second microprocessor. Another embodiment of the invention includes the first x-ray detector and the second x-ray detector being under a sample stream, wherein the x-ray tube, the first collimator and the second collimator are positioned above the sample stream, so that collimated x-rays are received by the x-ray detectors. Yet another embodiment of the invention includes the first x-ray detector and the second x-ray detector being above a sample stream, wherein the x-ray tube, the first collimator and the second collimator are positioned under the sample stream, so that collimated x-rays are received by the x-ray detectors. Still another embodiment of the invention is one in which the x-ray tube, the first collimator and the second collimator are positioned above a sample stream. Yet another embodiment of the invention further includes a first collection bin positioned to receive sample ejected by the first sized ejector, a second collection bin positioned to receive sample ejected by the second sized ejector, a first screen attached within the first collection bin, wherein the first screen defines a plurality of openings so that smaller sized objects may pass through the openings, a second screen attached within the second collection bin, wherein the second screen defines a plurality of openings so that smaller sized objects may pass through the openings. In another embodiment of the invention the first collection bin and the second collection bin are combined. Still another embodiment of the invention further includes a third x-ray detector, wherein the third x-ray detector is in a fixed position to receive x-rays collimated by the third collimator, a third microprocessor operationally connected to the third x-ray detector. Certain other embodiments of the invention further include an infrared 3D imager positioned above a conveyor so that identifying characteristics of pieces of the sample on the conveyor are determined.

Another embodiment of the invention is a method of sorting materials, measuring sorting efficiency and product purity including providing a sample, receiving a first collimated x-ray beam from an x-ray tube by a first detector, determining measurements of x-ray absorption of pieces of the sample, identifying the sizes of pieces in the sample having a higher density than coal, recording the size distribution from the first detector in a microprocessor, sorting the large pieces from the sample into a reject bin by use of an ejector, receiving a second collimated x-ray beam from the x-ray tube by a second detector located at an entrance to product bin, determining measurements of x-ray absorption of the remaining pieces of the sample, identifying the sizes of pieces in the sample having a higher density than coal, recording the size distribution of absorbing pieces detected by the second detector in the microprocessor, and determining ejections efficiency by comparing the two size distributions. Yet another embodiment of the invention further includes determining the number and sizes of absorbing pieces in the reject bin. Still another embodiment of the invention further includes positioning the first detector and the second detector under the sample stream. Yet another embodiment of the invention further includes protecting the first detector and the second detector with deflection plates. In another embodiment of the invention the sorting device further includes a deflection plate positioned so that the deflection plate defines a lower edge of the sample stream in order to protect each x-ray detector from direct contact with the sample stream.

Yet another embodiment of the invention is a method of measuring sorting efficiency and product purity including providing a sample, receiving a collimated x-ray beam from an x-ray tube by a detector, determining measurements of x-ray absorption of pieces of the sample, identifying the sizes of pieces in the sample having a higher density than coal, recording the size distribution and number of items detected by the detector. Still another embodiment of the invention is a method of protecting x-ray detectors while processing coal and other minerals including providing an x-ray detector, providing a diamond coated deflection plate, and positioning the diamond coated deflection plate to protect the x-ray detector in order to deflect any sample items that may contact the x-ray detector during processing of coal and other minerals.

Accordingly, one provision of the invention is to provide a method of sorting coal ore from contaminants into multiple fractions.

Still another provision of the invention is to provide methods of using x-ray energies for multi-fractional sorting of materials.

Yet another provision of the invention is to provide a multi-fractional coal sorting device.

BRIEF DESCRIPTION OF THE DRAWINGS

FIG. 5A shows a screen with smaller openings which allow coal fines to pass therethrough. FIG. 5B shows a screen having larger openings which allow smaller rock and ejected coal to pass through.

FIG. 9 shows the linear absorption coefficients from the National Institute of Standards and Technology for iron pyrite (FeS), coal, and silicon dioxide ($SiO_2$) over a range of x-ray energies. Also shown are their densities. Coal differs from mine to mine and even within the same coal vine; there is no standard definition for coal. The absorption shown for coal is the NIST value for graphite reduced to the 1.2 density of typical bituminous coal.

DETAILED DESCRIPTION OF THE INVENTION

Figure 1:
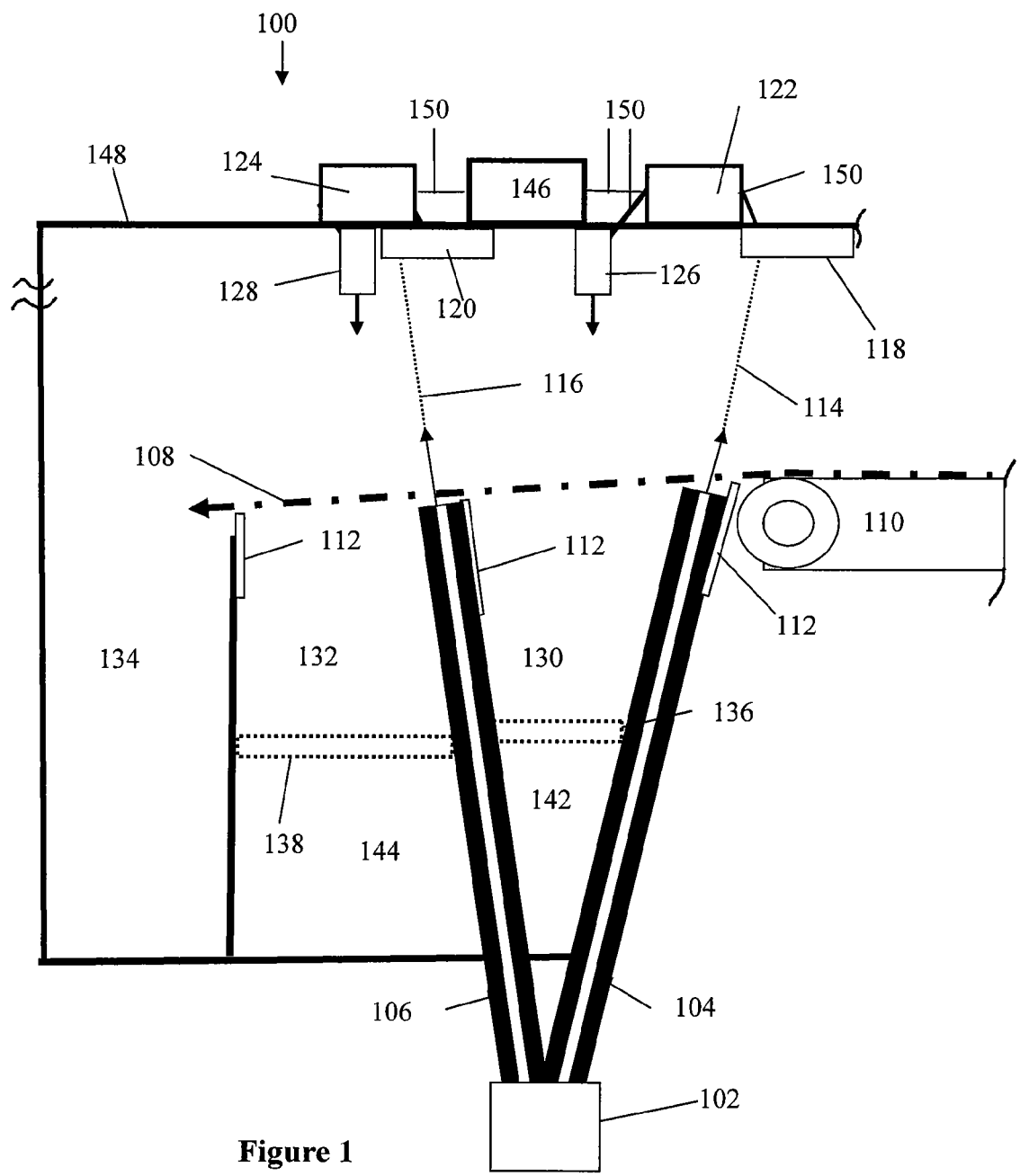
FIG. 1 shows a schematic diagram of a side view of an embodiment of a device for practicing the methods disclosed herein. Shown therein is a conveyor belt for transporting coal into a path between an x-ray source attached to a first and second collimator, and first and second x-ray detectors to receive the collimated x-rays. Also shown is a computer and ejector system for separating the coal into the areas shown. The collimated narrow x-ray beam fans perpendicular and under the sample stream.

The present invention discloses a device 100 for and methods of sorting contaminants away from coal. The device 100 and methods disclose the use of specific x-ray energies to detect contaminants of different sizes so that such large and small materials may be effectively sorted away from other pieces of coal not having contaminants. Briefly, the device 100 disclosed herein includes an x-ray source 102 and collimators so that x-rays are collimated into a narrow fan which is directed at x-ray detectors. This narrow fan uses only a small portion of the total x-rays which are produced over a wide range of angles from the x-ray target. The present invention uses three different x-ray fans from the same tube. Each collimated x-ray beam hits a separate detector which can control separate air jets. This permits a strong air blast from a large air ejector to remove large rock and a much smaller air blast from a small ejector to remove small rock impurities.

The methods disclosed herein include the steps of receiving collimated x-ray beams in order to determine x-ray absorption measurements of a sample, identifying small and large pieces of contaminant in the sample, and removing those small and large objects by the use of ejectors having different and appropriate force. The methods are performed at a very fast rate.

The methods disclosed herein may be used to "clean" coal so that sulfur, mercury, and the like, are reduced when the coal is used at a coal burning power plant. There are several benefits from the use of methods of removing contaminants from coal in order to provide a cost effective dry method to significantly reduce the amount of contaminants (for example, sulfur) below the levels available with current washing techniques. For example, cleaner coal improves boiler performance by reducing slag and corrosion problems. Also the herein disclosed dry processing method reduces the amount of water used in processing coal for washing reducing requirements for waste water treatment. Further, the "clean" coal's higher heating value increases boiler capacity. Also, the total amount of ash is reduced and less sensible heat is lost to moisture and the bottom ash. Accordingly, the methods disclosed herein provide cost effective methods to remove contaminants from coal in a size fractionated manner. The present invention takes into account that larger rocks require stronger air blasts than needed for smaller rocks. Sizing the air blast to the size of the rock saves compressor power and reduces the loss of coal adjacent to the rock.

By way of background, x-ray absorption in a material is a function of the density and atomic number of the material and it is also a function of the energy of the incident x-rays. A given piece of material will absorb x-rays to differing degrees depending upon the energy of the incident x-rays. Materials of differing atomic numbers will absorb x-rays differently. For example, materials having a higher atomic number will absorb x-rays much more readily than will materials having a lower atomic number. Also, the absorption profile of a given material over a range of x-ray energies will be different than the absorption profile of another material over that same range of energies. X-ray transmission through a material is given by the equation $N_{(t)} = N_0 e^{-\eta \rho t}$, where $N_{(t)}$ is the number of photons remaining from an initial $N_0$ photons after traveling through thickness t in a material of density $\rho$. The mass attenuation coefficient $\eta$ n is a property of the given material and has a dependence upon photon energy. The value $\eta \rho$ is referred to as the linear absorption coefficient ($\mu$) for a given material. Values of the coefficient $\mu$ have been established by researchers to high accuracy for most materials and these values are dependent upon the energy of incident x-ray photons. Values of $\mu/\rho$ (=$\eta$) for most elements can be found at the National Institute of Standards and Technology (NIST) internet website. The lists of values are extensive covering all stable elements for various values of photon energy (for example, a kilo electron volt, abbreviated as KeV). The value of $\rho$ for a given material is simply its density in gram/cm$^3$ and can be found in many textbooks and also at the NIST website. The ratio $N_{(t)}/N_0$ is the transmittance of photons through a thickness t of material and is often given as a percentage, i.e. the percentage of photons transmitted through the material.

In certain embodiments of the present invention, the device 100 for and method of sorting materials includes providing a sample, setting the detection thresholds, and sorting the sample according to the sorting parameters. Disclosed herein are the various embodiments for practicing the methods disclosed. By way of background, U.S. Patents for various x-ray measuring systems include 8,144,831 issued to Sommer, et al. on Mar. 27, 2012; 7,848,484 issued to Sommer, et al. on Dec. 7, 2010; 7,564,943 issued to Sommer, et al. on Jul. 21, 2009; 7,099,433 issued to Sommer, et al. on Aug. 29, 2006; RE36537 issued to Sommer et al. on Feb. 1, 2000; 5,738,224 issued to Sommer et al. on Apr. 14, 1998; 7,664,225 issued to Klein on Feb. 16, 2010; 6,338,305 issued to McHenry, et al. on Jan. 15, 2002; 7,542,873 issued to Vince, et al. on Jun. 2, 2009; 7,200,200 issued to Laurila, et al. on Apr. 3, 2007; 5,818,899 issued to Connolly, et al. on Oct. 6, 1998; 4,486,894 issued to Page, et al. on Dec. 4, 1984; 4,090,074 issued to Watt, et al. on May 16, 1978; 4,377,392 issued to Massey, et al. on Mar. 22, 1983, and U.S. Patent Application Publication No. 2010/0219109 to Roos, et al. on Sep. 2, 2010, each of which is hereby incorporated by reference in its entirety.

As an initial matter, in certain embodiments, providing the sample may include providing run of mine ore from a coal mine. In other embodiments, the sample may be coal that has already been subjected to some cleaning method or procedure. In still other embodiments, the sample to be subjected to the methods disclosed herein may be any ore material containing a contaminant. By way of illustration, but not limitation, examples of contaminants include sulfur, mercury, silicates, carbonates, iron, calcium, aluminum, and the like. Further, mining ores are often silicates with metallic inclusions. The metallic inclusions have higher linear x-ray absorption coefficients. Accordingly, if gold ore is crushed, then the small gold inclusions could be detected and ejected by use of the present methods.

Referring now to FIG. 1, there is shown an embodiment of the present invention. When referred to herein, x-ray source 102, means a source of x-rays, such as an x-ray tube, or the like, as known to those in the industry. The embodiment includes an x-ray source 102, first collimator 104 and second collimator 106 located under a sample stream 108 flying off conveyor 110 and clears splitter plates 112. The sample stream 108 may, in certain embodiments, also be referred to as a mineral or coal stream. Said collimators produce x-ray fans 114 and 116 that strike a first x-ray detector 118 and a second x-ray detector 120, respectively, which measure the absorption by the sample stream 108. Each x-ray detector 118 and 120 send signals to the first microprocessor 122 and second microprocessor 124, respectively, which communicate with and control the first sized ejector 126 and second sized ejector 128, respectively, that deflect selected objects from the sample stream 108 into bins 130 and 132. A structural support 148 is used to mount detectors 118 and 120, ejectors 126 and 128, microprocessors 122 and 124, as well as other equipment, such as a computer 146, as needed in a given embodiment. Those of ordinary skill in the art are familiar with suitable materials, and positioning of the same, as disclosed herein. Also shown are communication connections 150, such as data cables, and the like, as known to those of ordinary skill in the art, for the necessary electrical, data and information transfer between the various components. Throughout this application, it is understood that the necessary electrical, data and information transfer connections are in place between the various components whether or not such operational connections are shown in the figures. Further, given the schematic nature of the figures, such operational connections are understood to be represented. The first microprocessor 122 selects for ejection large dense rock in the sample stream 108 and the first sized ejector 126 deflects the selected item into bin 130 where it strikes a first screen 136 having openings 140 that allow undersized items to pass into bin 142 where they can be returned to the conveyor 110. It is understood that the first sized ejector 126 will deflect a mixture of rock and coal fines. The impacts of the rock on these screens cause vibrations which facilitate the separation of the coal fines from the ejected rock. The second collimated x-ray beam 116 strikes an x-ray detector 120 which detects x-ray absorption by the smaller rocks in the sample stream 108 and the second microprocessor 124 sends a signal to the second sized ejector 128 in order to deflect the smaller rocks into bin 132 and on to a screen 138, which has openings 140 sized to recover fine coal. The fine coal is collected in bin 144 and can be transferred to sorted coal bin 134. The data from the microprocessors 122 and 124 is analyzed by the computer 146 and is used to adjust and measure the performance of the device 100.

Still referring to FIG. 1, as the sample stream 108 passes between the x-ray source 102 and the x-ray detector 118 the sample is irradiated. The x-ray detector 118 is operationally connected by connection 150 to a first microprocessor 122, also called a computer, which directs first sized ejector 126 to send contaminated coal to bin 130. As used herein, microprocessor is referring to a computer, or the like to serve the stated function. Coal that is not ejected is collected in bin 134. As previously disclosed herein, the microprocessor has software, or other means in order to perform the steps indicated herein. In certain embodiments, the determination may be as simple as material having an atomic number of greater than 6.

Regarding the manufacture and use of collimators, methods are well known in the industry for making a suitable collimators as described herein. An example of a material which a collimator is made of is steel, having a thickness of 5 mm with an opening of a quarter inch through which the x-rays pass. In other embodiments, collimators may be manufactured of lead or brass and sized as needed. One of ordinary skill in the art is familiar with such collimators Use of a collimator with x-rays is beneficial because they reduce scattered x-rays. In the embodiments shown herein, the collimators are attached to the x-ray source 102 by bolts and also attach to framework or supports (not shown) of the collection bins. Alternatively, the collimators may be attached to x-ray tube 102 housing by means as known to those of skill in the art.

A meaningful difference in force produced exists between the first sized ejector 126 and the second sized ejector 128. The air ejector force required to deflect a large rock is much greater than the air blast needed to remove the smaller objects. The air blast that can remove a large rock will also remove a portion of the coal that surrounds it. If the same air blast is used for all detected rock sizes there is too much loss of fuel product. Accordingly, smaller sized air ejectors in an air ejector array are spaced closer together than are larger ejectors and have an air blast profile that is smaller in area and smaller in force than the air blast profile from the larger ejector. Larger sized contaminates are ejected using the larger ejectors and smaller sized contaminates are ejected using the smaller ejectors. If only large ejectors spaced for example at 1 inch spacing are used and if the rock size selected for removal is limited to rocks greater than one inch, it can provide a 70% or greater removal of rock. This has substantial benefits in reducing the transportation costs to send ROM coal from the mine to a typical washing system located near a water source. The removal of large rock still gives a coal product with substantial impurities, which needs further processing. By way of background, coal typically has a specific gravity of 1.2 while the rock and heavier minerals have average values of 2.5.

Still referring to the methods disclosed herein, after a decision is made that a contaminant is present and should be ejected, then next determination regards what amount of area needs to be ejected with the appropriate large or small ejectors selected to eject the contaminant. Some x-ray sensing devices have a capacity of 32 linear pixels per inch. Other x-ray sensing devices have a capacity of 64 linear pixels per inch. The ejection area size may be set based upon a required number of pixels detecting a contaminant. For example, if a device having 32 linear pixels per inch is in use which are read 32 times as the sample travels one inch in passing between the x-ray source 102 and the detector and it is desired to eject areas of one square inch, then it could be required that up to 1024 contiguous pixels would need to detect a contaminant in order for the air ejector to be triggered to take action. The number of contiguous pixel readings having reduced x-ray transmissions required to initiate a blast of air for ejection determines the minimum size of the ejected contaminant. The required pixel number is an adjustable perimeter within the method. With the example above, one of ordinary skill in the art may adjust the perimeter to their specific needs. Accordingly, if economic value is provided by removing smaller contaminant inclusions, then the methods disclosed herein may be used. In still other embodiments, the percentage transmission information is saved by the machine and used to normalize the voltage output of each pixel in the x-ray detector array. The pixel number and the percentage of the threshold are adjustable perimeters that can be set manually, or automatically in the x-ray measuring device.

The smaller impurities often include iron pyrite which contains some 80% of the toxic mercury and other heavy metal sulfides. Removal of insoluble mercuric sulfite at the mine has substantial economic and environmental benefits. The present invention may provide the benefits of washed coal at higher speeds without water. It can permit the production of clean coal directly from ROM coal at the mine. Rock impurities are not contaminated by the heavy media and the dry process can free operators from the requirement of trucking rock which is expensive.

Figure 2:
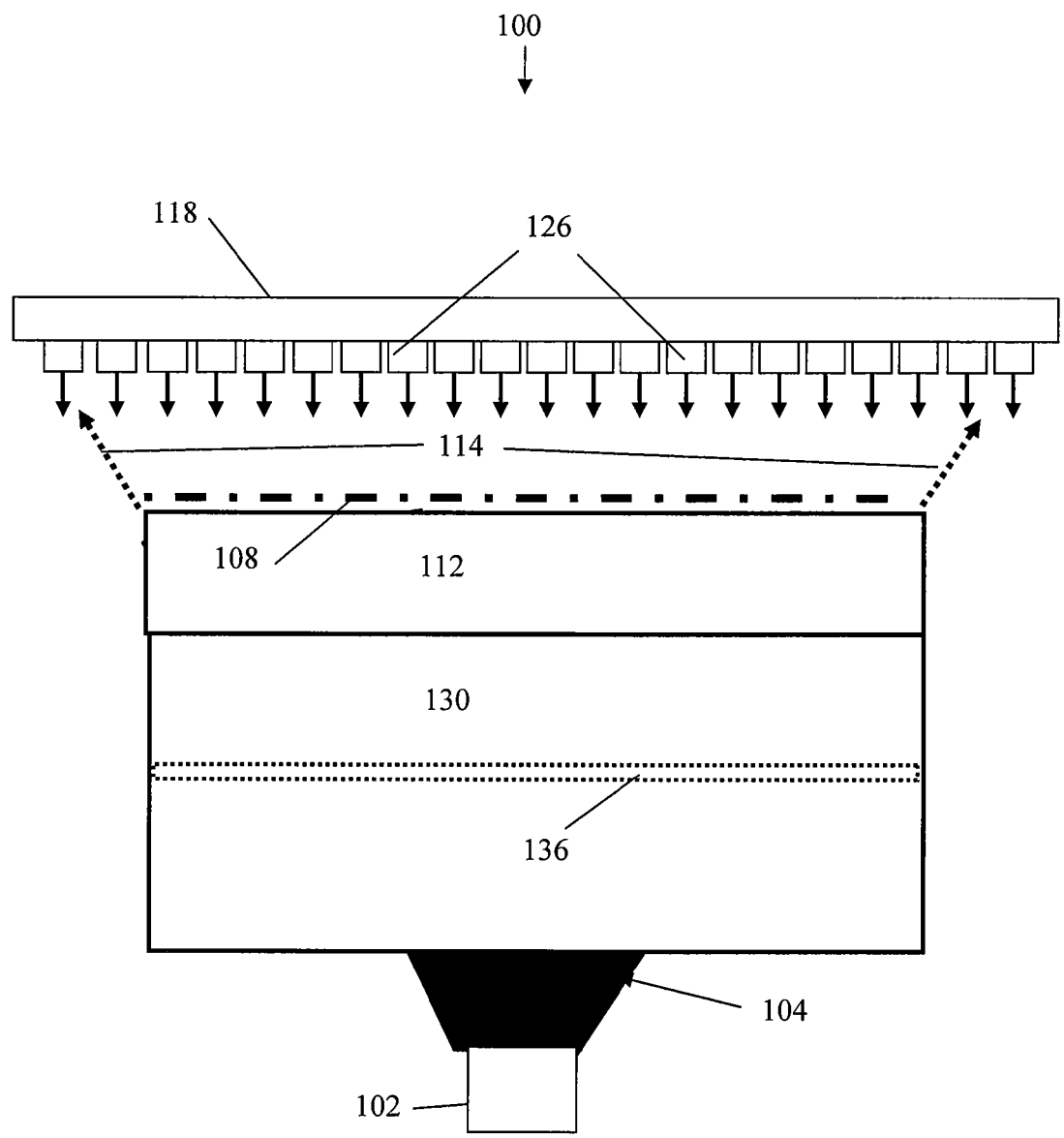
FIG. 2 is a front view of a schematic diagram of an embodiment of a device for practicing the methods disclosed herein. Specifically, shown therein is an x-ray source and collimator positioned beneath the sample stream. The x-ray detectors and first sized ejectors are positioned above the sample stream. The downward pointing black arrows represent air blasts for deflecting identified sample into the collection bin shown. The collimated narrow x-ray beam fans parallel to and under the sample stream.

Referring now to FIG. 2, there is shown an embodiment of the device 100 having an x-ray source 102 and collimator 104 located under a sample stream 108 that clears splitter plate 112. The collimated x-ray fan 114 strikes the first x-ray detectors 118 which detect the absorption by the larger rocks in the sample stream 108. The first x-ray detector 118 sends a signal to the first sized ejectors 126 that deflect the rocks into bin 130 and on to a screen 136 (shown in phantom lines) with openings 140 sized to recover small sizes.

Figure 3:
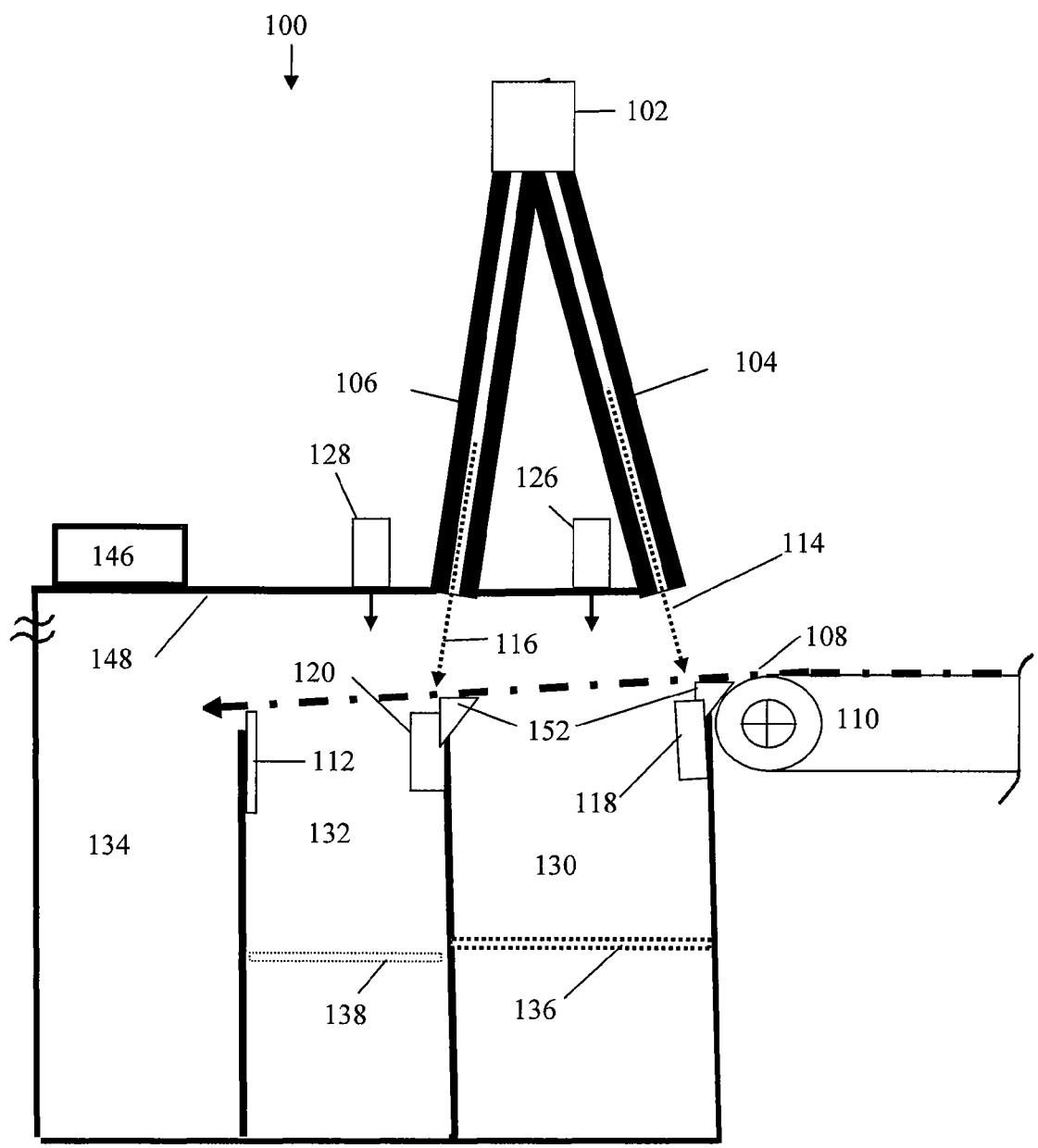
FIG. 3 shows a schematic diagram of a side view of an embodiment of a device for practicing the methods disclosed herein. Shown therein is a conveyor belt for transporting coal into a path between an x-ray source attached to a first and second collimator, and first and second x-ray detectors to receive the collimated x-rays. Also shown is a computer and ejector system for separating the coal into the areas shown. The collimated narrow x-ray beam fans perpendicular and above the sample stream.

FIG. 3 shows an embodiment of the present invention in which the x-ray source 102, first collimator 104 and second collimator 106 are located above the sample stream 108 that flies off a conveyor 110. The first collimated x-ray fan 114 strikes the first x-ray detector 118 which detects the absorption by the larger rocks in the sample stream 108. The first x-ray detector 118 sends a signal to the first sized ejector 126 for large rocks that deflects the rocks into bin 130 and on to a first screen 136 having openings 140 sized to recover small sizes. The second collimated x-ray fan 116 strikes a second x-ray detector 120 which detects the absorption by the smaller rocks in the sample stream 108 and sends a signal to the second sized ejector 128 for small rocks that deflects said rocks into bin 132 and on to a second screen 138 with openings 140 sized to recover fine coal. The coal in the sample stream 108 passes over the splitter plate 112 and is collected in bin 134. Also shown is computer 146 which is operationally connected to the microprocessors 122 and 124 (not shown) for recording data and performing other functions as disclosed herein. For the understanding of the Examiner, Applicants note that the first microprocessor 122 of the first x-ray detector 118 is located at the same location that the detector 118 is shown. Also, the second microprocessor 124 of the second x-ray detector 120 is located at the location that the detector 120 is shown. Electrical and data communication connections which exist between the computer 146, detectors 118 and 120 and ejectors 126 and 128 are not shown.

Still referring to FIG. 3, there is shown an embodiment of a device 100 for practicing the methods disclosed herein further including a deflection plate 152. This plate 152 is shown in detail in FIG. 11. In certain embodiments of the invention, the diamond coated deflection plate 152 includes a bar, also called a body, that is bolted to the frame of the device 100 and a diamond coated plastic film or diamond coated metal foil that lies over an x-ray detector window 158 shown in FIG. 11. The body of the deflection plate 152 acts to prevent an item in the sample stream 108 from contacting a detector, such as detector 118. In certain embodiments, a flat body shape in alignment with the flow of the sample stream 108 is desired. The deflection plate 152 functions to protect the x-ray detectors 118 and 120, electronics, or other equipment that may be positioned under, or beneath, the sample stream 108. That is, the deflection plate 152 establishes the lower boundary of the sample stream 108, so that items under that lower boundary are not inadvertently struck by something in the sample stream 108. In certain embodiments, the deflection plate 152 is a steel plate with a heat treated diamond coating. The deflection plate 152 protects the detector window 158 (shown in detail in FIG. 11) of the x-ray detector 118 from the coal stream 108. In another embodiment the deflection plate 152 includes a diamond coated steel bar and a diamond coated plastic window. The deflection plate 152 defines the lower portion of the coal stream 108. It protects the window 158 while allowing x-rays 114 to pass through the diamond coated plastic window 154 portion of the deflection plate 152 and window 158 to interact with the detector 118. The use of vapor deposited carbon to provide a diamond coating is well known to those skilled in the art and such services are readily commercially available. It is even used to coat skillets and other cookware. This coating is abrasion resistant and has x-ray absorption comparable to coal. It has better abrasion resistance than tool steel. In other embodiments, the deflection plate 152 may be constructed of material suitable for the function disclosed herein, such as tool steel or ceramics. The deflection plate 152 permits the sensitive portions of the x-ray detector 118 to withstand the bombardment by portions of the sample stream 108. It also will allow placement of the detector 118 on the edge of the coal stream 108 for a reduction in required x-ray power and an increase in the signal to noise levels.

Several different embodiments of the present invention are shown. Two different orientations of the x-ray beams are shown in FIGS. 1 and 3. The larger rock sizes are first removed from the sample stream 108 and then a second set of x-ray detectors 120 control the second sized ejectors 128 to remove the smaller impurities. FIG. 2 shows the x-ray fan from an x-ray tube 102 mounted under the sample stream 108 from a high speed conveyor 110. FIG. 3 shows the x-ray tube 102 mounted above the sample stream 108.

Figure 4:
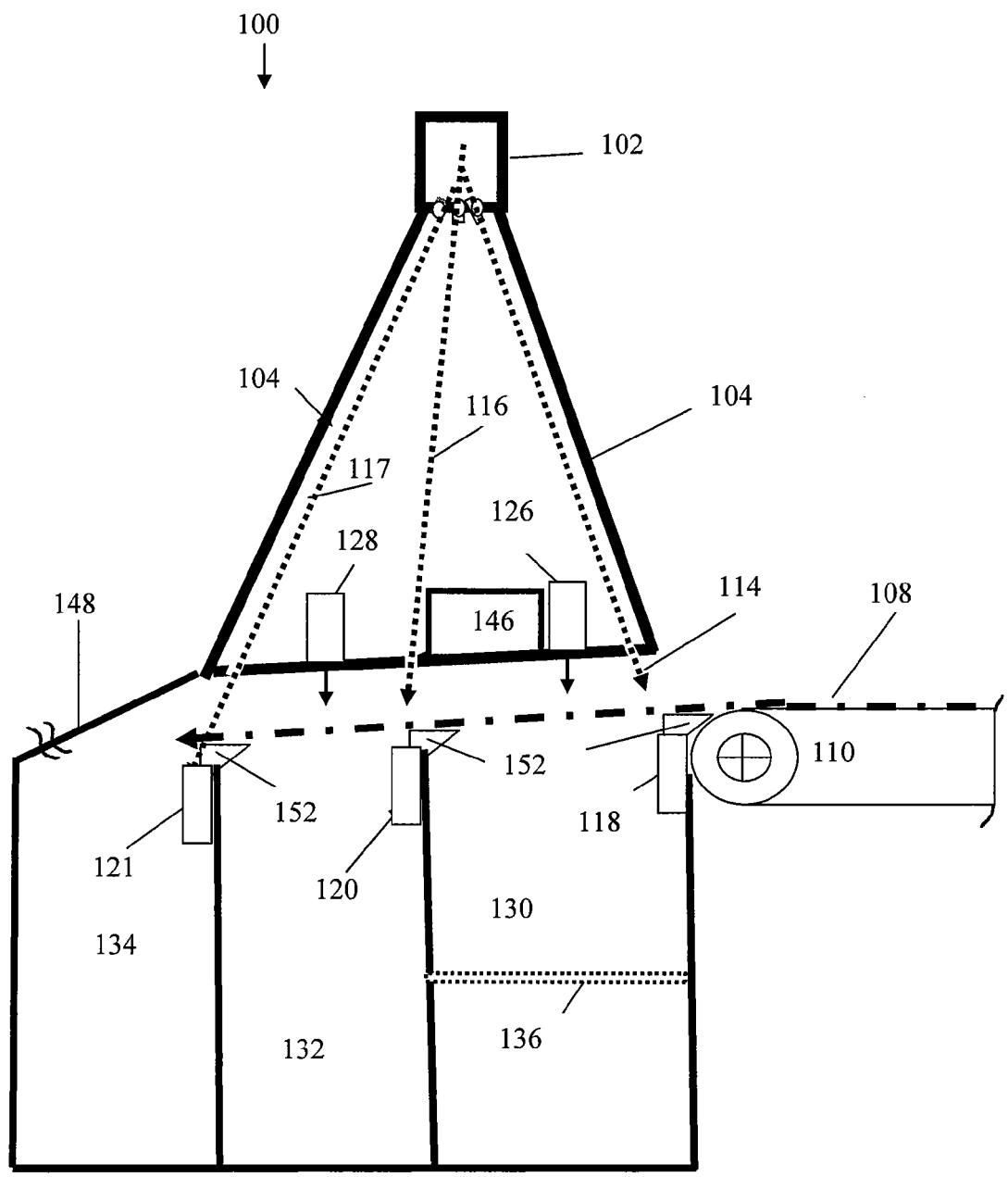
FIG. 4 shows a schematic diagram of a side view of an embodiment of a device for practicing the methods disclosed herein. Shown therein is a conveyor belt for transporting coal into a path between an x-ray source attached to first collimator located above the sample stream, and first, second and third x-ray detectors located below the sample stream to receive the collimated x-rays. Also shown are the two sizes of ejectors for separating the rocks and coal into the areas shown. The computer uses the data from the three detectors to measure sorting efficiency. From the single collimator there are multiple collimated narrow x-ray beam fans perpendicular and above the sample stream.

Referring now to FIG. 4, there is shown an embodiment of the present invention in which an x-ray source 102 and a single collimator 104 produce the collimated x-ray fans 114, 116, 117 which are located over a sample stream 108 flying off conveyor 110. In certain embodiments, the collimator 104 is a single closed structure, except for the openings which allow passage of x-ray beams. With such a construction, other items, such as a computer 146, may be placed inside of the structure. The collimated x-ray fans 114, 116, 117 strike the x-ray detectors 118, 120, 121, respectively, which detect the absorption by items in the sample stream 108. The x-ray detectors 118, 120, 121 send measurements to microprocessors 122, 124, 125. Those microprocessors 122, 124, 125 are at the same location in schematic FIG. 4 as their corresponding detectors 118, 120, 121, respectively. In alternate embodiments, a system of processors (not shown) may be used. The microprocessors, or system of processors process the measurements and send signals to the first sized ejector 126, and second sized ejector 128, respectively, that deflect appropriately sized items into bins 130, 132, and 134. The computer 146 uses the detected signals to measure the number and size of each detected particle in the three bins 130, 132 and 134. In the same manner that the screens are used above, within bin 130 is a first screen 136, and within bin 132 is a second screen 138, each having openings 140 sized to recover small sizes. Still referring to FIG. 4, there are three openings in the collimator 104 housing near the x-ray tube 102 and a second set of three openings in the collimator 104 housing at the base which holds the ejectors 126 and 128. These openings are all parts of the collimator 104 and x-ray beams 114, 116, 117 are shown to pass through them.

Figure 5A:
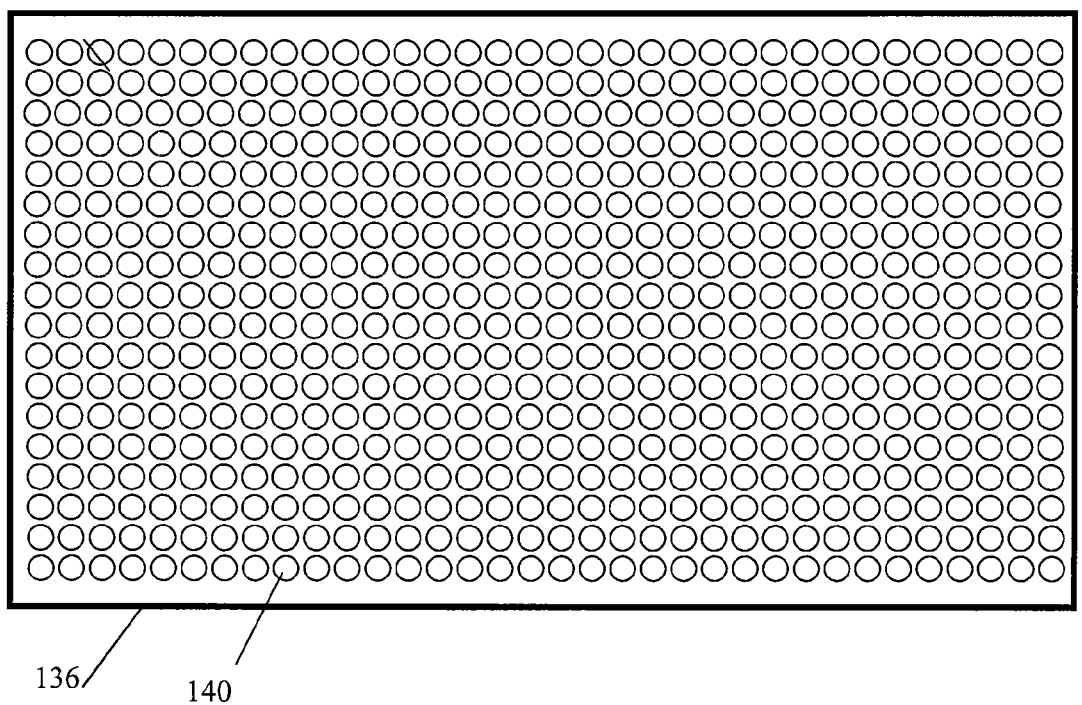
FIG. 5A-5B shows schematic diagrams of embodiments of the recovery screens used in connection with the present invention.
Figure 5B:
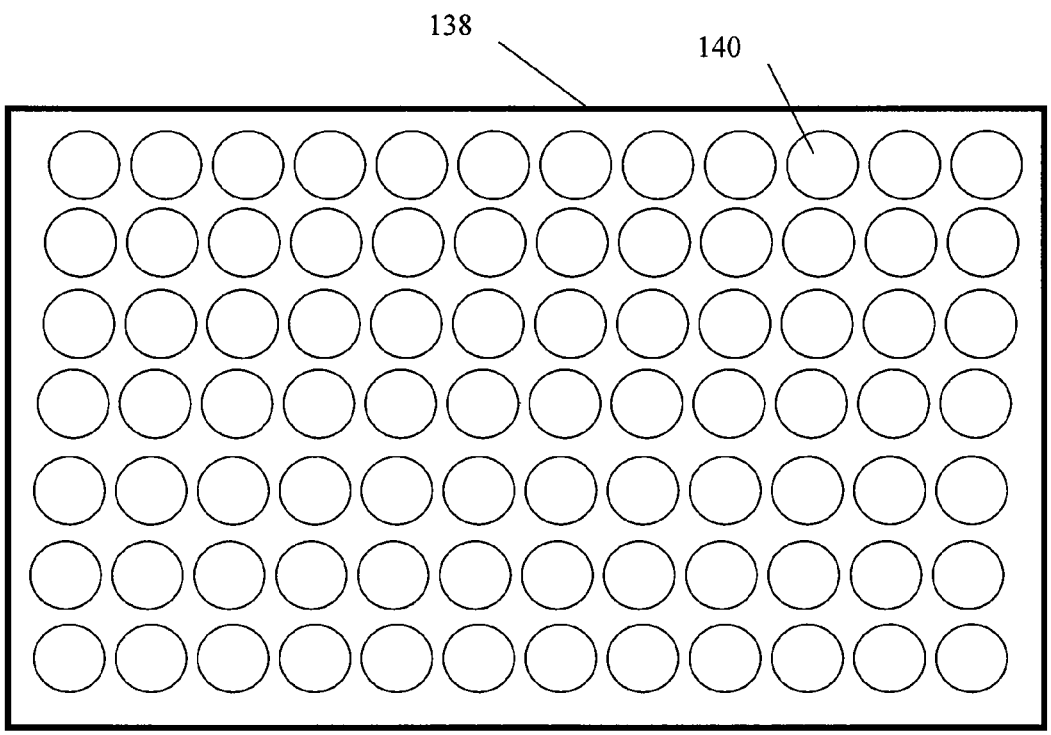

FIG. 5A-5B shows an embodiment of the first screen 136 and the second screen 138. In FIG. 5A the screen 136 with the smaller openings 140 recovers the fine coal ejected with the smaller rocks and reduces product loss. In FIG. 5B the recovery screen 138 with openings 140 sized to recover smaller rocks and coal ejected with the large rocks. The openings 140 allow smaller rock and coal to pass therethrough, which can be returned to the sample stream 108 for further separation.

Figure 6:
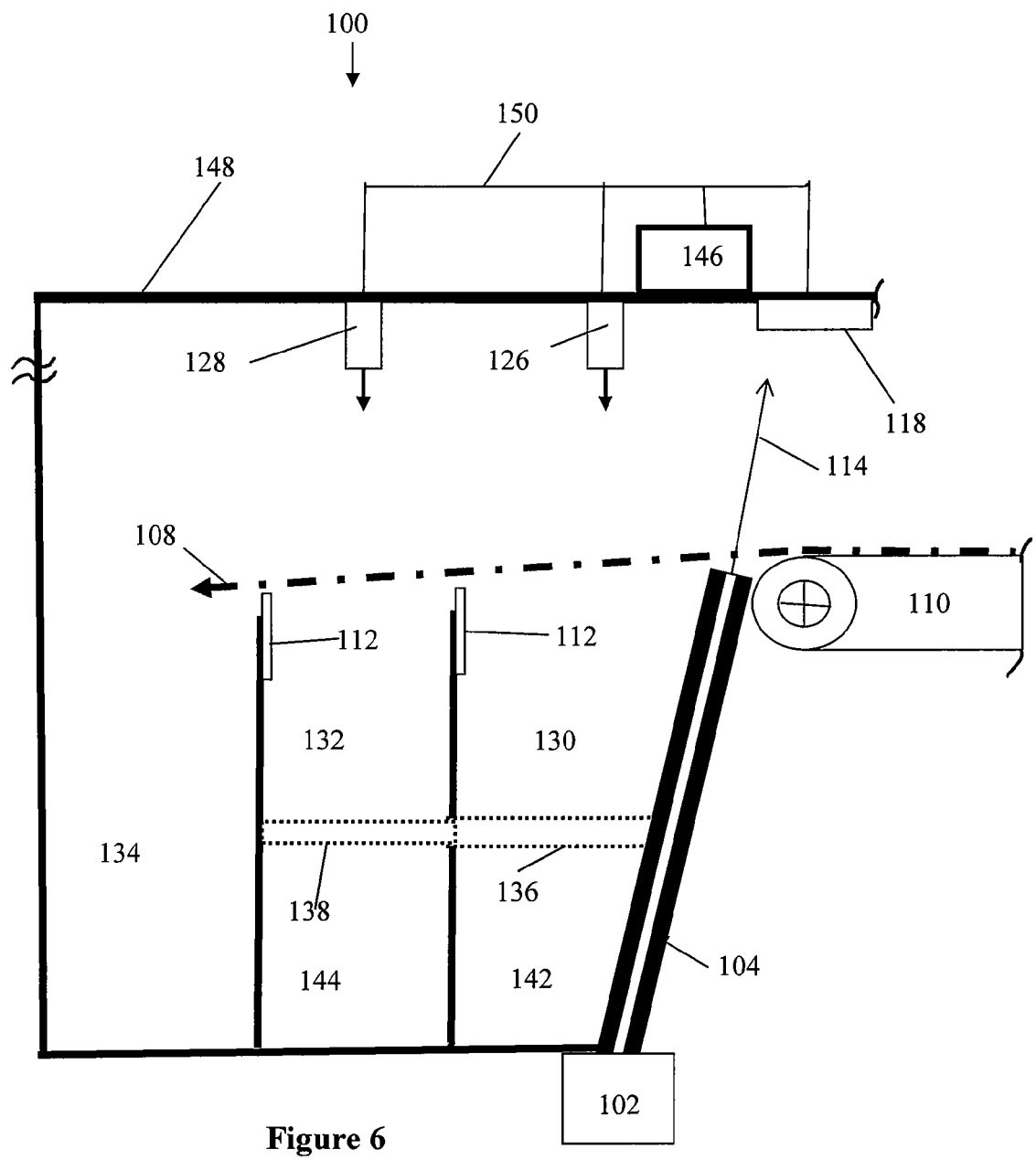
FIG. 6 shows a schematic diagram of a side view of an embodiment of a device for practicing the methods disclosed herein. Shown therein is a conveyor belt for transporting coal into a path between an x-ray source attached to a first collimator located beneath the sample stream, and a first x-ray detector located above the sample stream to receive the collimated x-rays. Also shown are the two sizes of ejectors for separating the rocks and coal into the areas shown. All of the ejectors are controlled by a single microprocessor. In sum a dual ejector system with single collimated x-ray beam fan perpendicular and under the sample stream is shown.

Referring now to FIG. 6, there is shown an embodiment of the present invention in which a single x-ray detector 118 operates both a first sized ejector 126 and a second sized ejector 128. Shown therein is an x-ray source 102 and first collimator 104 located under a sample stream 108 flying off the conveyor 110 and clearing splitter plates 112. The first collimator 104 produces an x-ray fan 114 that strikes a first x-ray detector 118 which measures the absorption by the sample stream 108. The first x-ray detector 118 sends signals to the first microprocessor 122, which is at the same location in the Figure as the detector 118, which controls the first sized ejectors 126 and the second sized ejectors 128 that deflect selected objects in the sample stream 108 into bins 130 and 132, respectively. Also shown are communication connections 150 and a support structure 148 to which detectors 118, ejectors 126, 128, or the like, may be attached. Specifically, the first microprocessor 122 selects for ejection of large dense rock in the sample stream 108 and the first sized ejector 126 deflects the selected items into bin 130 where they strikes the first screen 136 with openings 140 that pass undersized items into bin 142 where they can be returned to the conveyor 110. Also, the first microprocessor 122 selects smaller rocks for ejection and sends a signal to the second sized ejector 128 that deflects said rocks into bin 132 and on to a second screen 138 with openings 140 sized to recover fine coal. The fine coal is collected in bin 144 and can be transferred to the sorted coal bin 134.

An alternate to the embodiment shown in FIG. 6 could combine the multiple x-ray beams 114, 116 and 117 of FIG. 4 into a single x-ray beam so that only a single x-ray beam 114 exists. Similarly, an alternate embodiment could combine the multiple detectors 118, 120 and 121 into a single detector array—say 118, all connected through a single processor to ejectors 126 and 128 (which remain separated as shown in FIG. 4) to eject rocks of various and selected sizes into separated bins 130, 132 or 134 as appropriate.

Figure 7:
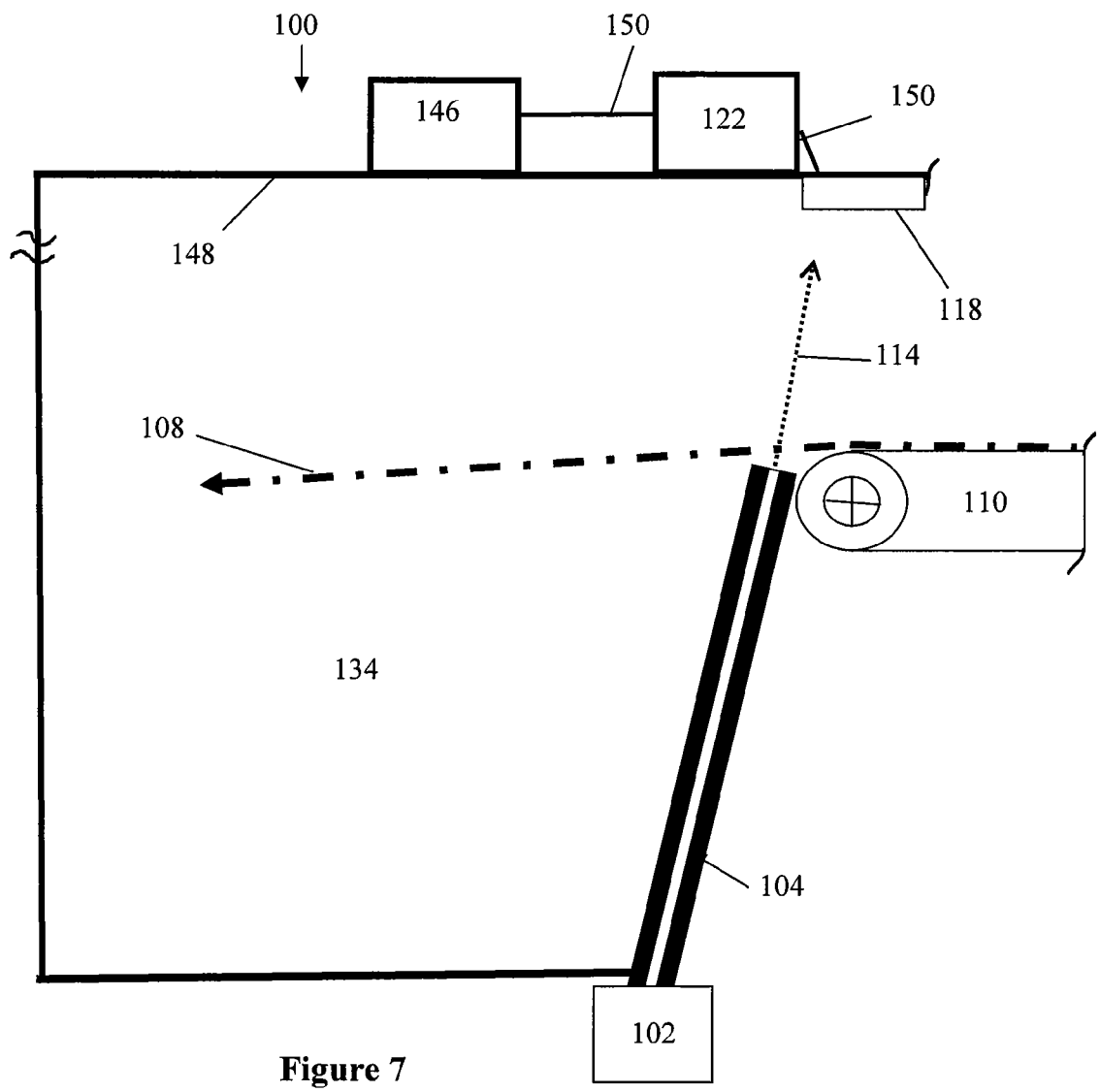
FIG. 7 shows a schematic diagram of a side view of an embodiment of a device for inspecting a sample, as disclosed herein. Shown therein is a conveyor belt for transporting coal into a path between an x-ray source attached to a first collimator located beneath the sample stream, and a first x-ray detector located above the sample stream to receive the collimated x-rays. The detector sends signals to a microprocessor which then transmits data to a monitor. The purpose of this embodiment is to inspect the amount of rock in a sample without sorting.

FIG. 7 shows an embodiment of the present invention for inspection of a sample. Shown therein is an x-ray source 102 and first collimator 104 are located under a sample stream 108 flying off conveyor 110. The first collimator 104 produces x-ray fans 114 that strike a first x-ray detector 118 which measure the absorption by the sample stream 108. The first x-ray detector 118 sends signals to the first microprocessor 122 which transmit to computer 146 the sizes and number of items detected by the detector 118. The coal and rock are collected in bin 134. As used herein, in certain embodiments, a bin 130, 132, 134 (FIG. 6) may also allow for placement on a conveyor belt. In this embodiment, it may be desired to collect the sample stream 108 on another conveyor.

Shown in FIG. 9 are the linear absorption coefficients from the National Institute of Standards and Technology (NIST) mass absorption coefficients ($\mu$) for iron pyrite (FeS), coal, and silicon dioxide ($SiO_2$) over a range of x-ray energies. Also shown are their densities. Note that coal is a mixture of carbon and hydrocarbons and there is no NIST "standard" for coal. Accordingly, the x-ray absorption coefficients of coal are the NIST data for graphite corrected for coal density of 1.2 grams per cubic centimeter (g/cc). As shown elsewhere herein, the absorption by coal is much less than the absorption of pyrite in silicates for 8 to 20 kilo electron volts (KeV) x-rays. Using the information in FIG. 9 illustrates how a contaminant can be differentiated from coal. For example, it is calculated that use of x-ray energy at a level of 15 KeV results in a 56.6% transmission through coal having a thickness of 1 cm, while contaminants having a thickness of only 1 mm have reduced transmission percentages of 0% (for FeS), and 20.5% (for $SiO_2$). By way of a second example, it is calculated that use of x-rays at an energy level of 20 KeV for which coal having a thickness of 1 cm has a transmission percentage of 73.2%, as compared to contaminants such as FeS and $SiO_2$ which have transmission percentages of 0% and 50%, respectively.

In certain embodiments of the present invention, the range of x-ray energies used is dependent upon the thickness of the sample stream 108. In certain embodiments, the range of x-ray energies may be from about 6 KeV to about 100 KeV. In other embodiments, the x-ray energies may be in the range of from about 8 KeV to about 20 KeV. In still other embodiments, the range of x-ray energies may be from about 50 KeV to about 100 KeV. In still other embodiments, the range of x-ray energies is above the absorption edge of the ejected element. Various devices may be appropriate to supply the x-ray energies and x-ray detectors used in the methods disclosed herein. In certain embodiments of the present invention, such a device may be the TruSort machine, second generation, commercially available from National Recovery Technologies, LLC of Nashville, Tenn. In other embodiments, an appropriate x-ray device is available from Commodas Mining GmbH at Feldstrasse 128, 22880 Wedel, Hamburg, Germany, and is called the CommodasUltrasort. It uses dual-energy detection algorithms similar to airport baggage scanners. In still other embodiments, an appropriate x-ray sensing device may be model no. DXRT which is commercially available from National Recovery Technologies, LLC of Nashville, Tenn. The x-ray sensing machine may be a dual energy device. In other embodiments of the present invention, the x-ray device may be a broadband x-ray device such as the vinyl cycle model, which is commercially available from National Recovery Technologies, LLC of Nashville, Tenn.

Figure 10:
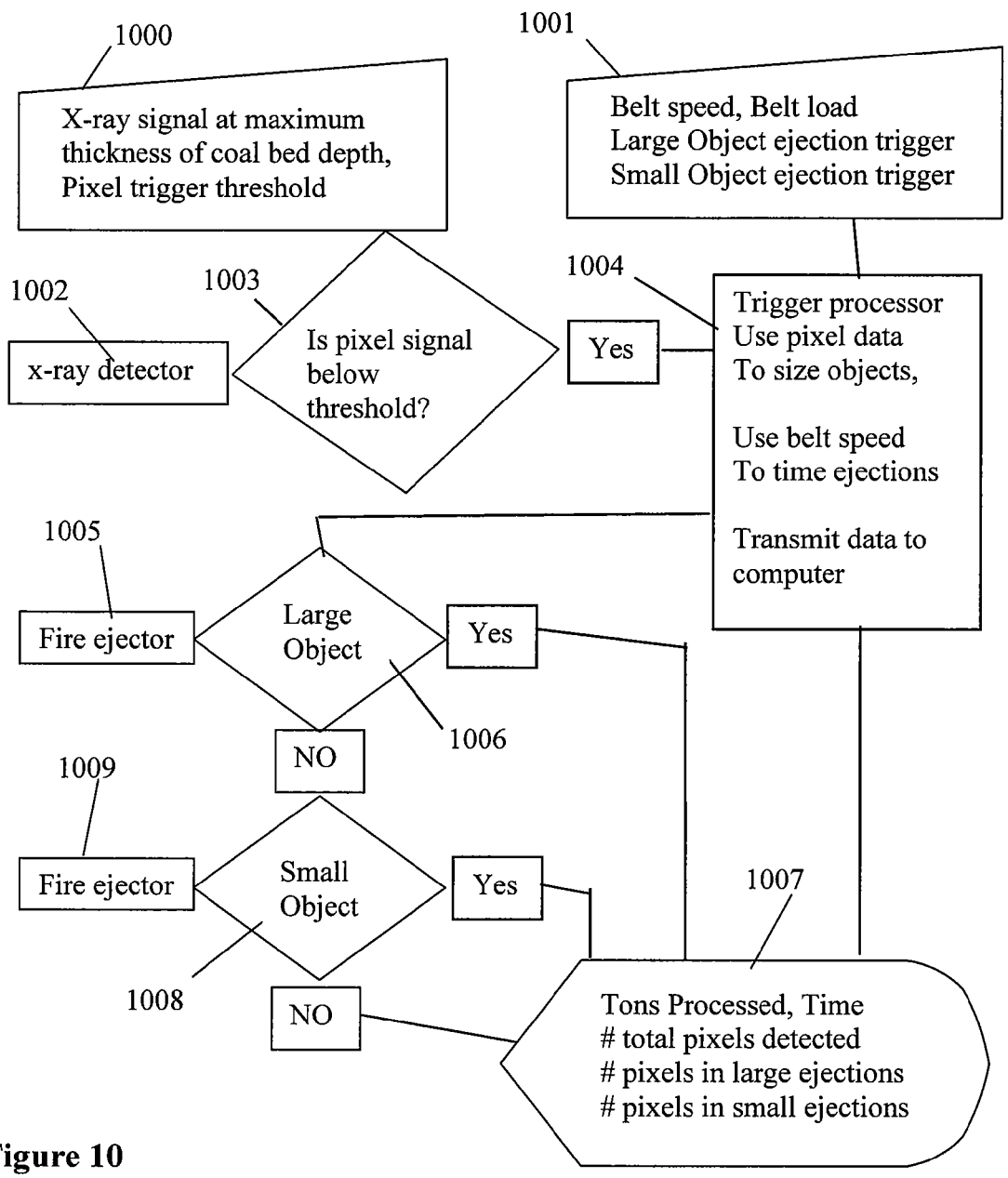
FIG. 10 shows a flow diagram of an algorithm that uses the number of pixels with high absorption during the cycle time of the x-ray detector.

FIG. 10 shows the schematic algorithm in one embodiment of the present invention which uses the number of detector pixels which detect absorption of x-rays above and below the preset threshold. This algorithm uses the ratio of total number of pixels during the recycle time of the x-ray detector array and the number of pixels reporting x-ray intensities below said threshold. Accordingly, in a certain embodiment, the pixel density is 32/inch and there are 1024 pixels readings while the coal passes one inch over the detector. The coal leaves the conveyor belt at 120 inches/sec and the x-ray detector (118, 120 or 121) array is read and reset 32 times during one inch of travel of the coal stream. If the air ejectors (126 or 128) are one inch apart each jet is controlled by the adjacent detectors providing 32 intensity measurements to the computer 146 each time it reads and resets the detector array. The operator can set the detector to only report readings that are less than a preset amount and indicate the presence of objects which absorb more than coal. The computer 146 can collect and analyze the data it collects and adjust the amount of ejected air. Larger items require more air than smaller items. The number of pixels reporting higher absorption is a measure of the size of the object and the amount of air required to eject it. Regarding FIG. 10, the operator inputs items 1000 and 1001. When in use, the x-ray detector 1002 reads sample and asks is the pixel signal below threshold 1003. If yes, then the computer 146 records information 1004. If a large object 1006 is detected, then a large air blast is provided by firing ejector 1005 and further information 1007 is stored. If a small object 1008 is detected, then a small air blast is provided by firing ejector 1009 and further information 1007 is stored.

Figure 11:
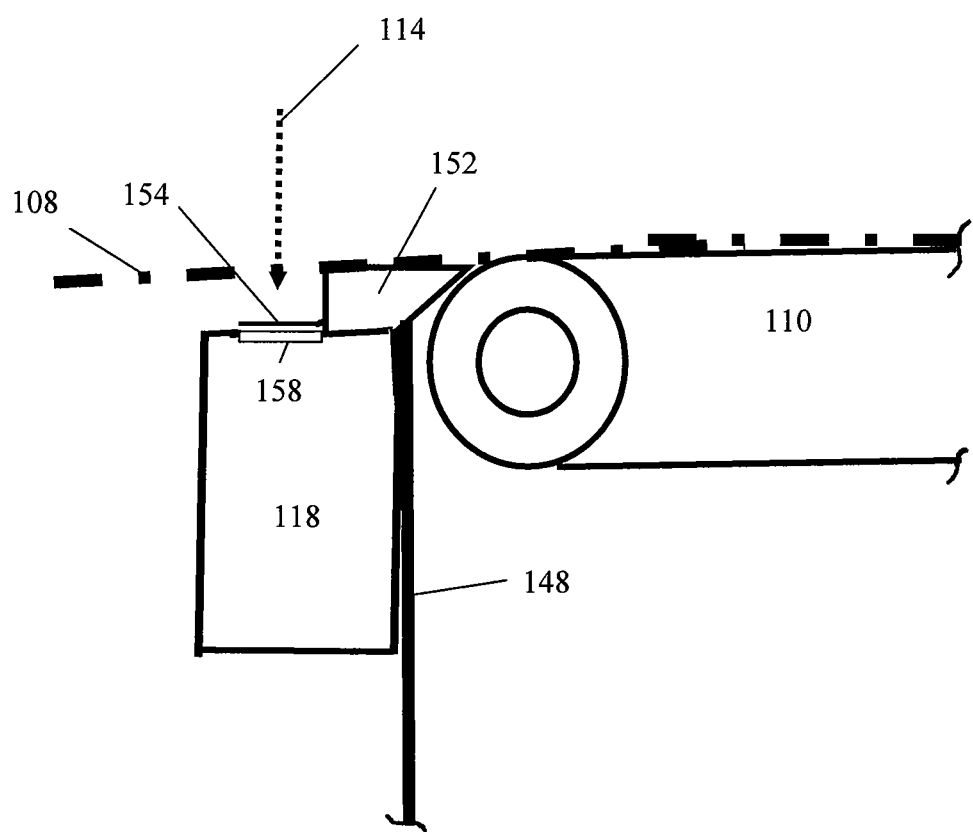
FIG. 11 shows an enlarged schematic diagram of the deflection plate which permits the x-ray detector to be located at the lower edge of the coal stream. Note that the positioning of the deflection plate prohibits the x-ray detector from being contacted by pieces in the sample stream.

FIG. 11 shows the deflection plate 152 referenced in FIG. 3 in larger detail. It shows that the deflection plate 152 is composed of a mechanical bar that prevents larger items in the coal stream 108 from striking the detector 118 and a diamond coated cover 154, also called a window, for the x-ray window 158 of the detector 118. In certain embodiments, the deflection plate 152 and the diamond coated cover 154 are attached to the x-ray detector 118 and the diamond coated plastic window 154 portion of the deflection plate 152 covers the x-ray window 158 of the detector 118. In other embodiments, the deflection plate 152 is attached to a support structure 148.

Figure 12:
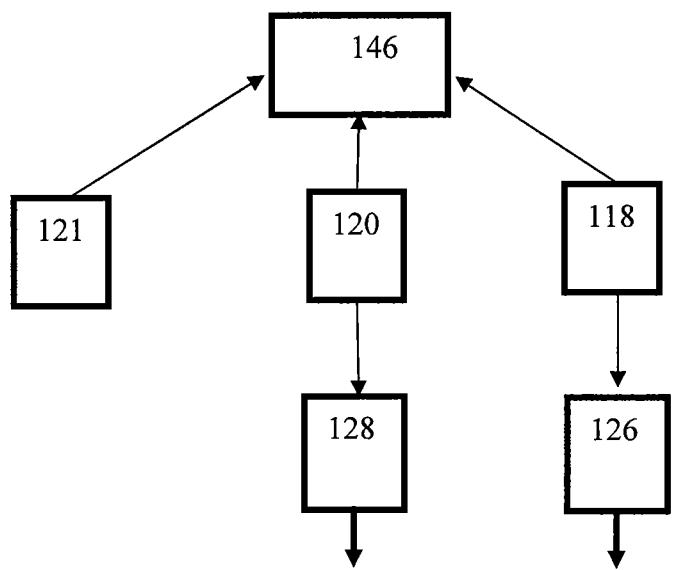
FIG. 12 is a schematic diagram showing the connections between the different x-ray detectors, ejectors and the computer shown in FIG. 4.

FIG. 12 shows the data flow from x-ray detectors 118, 120 and 121 to the computer 146 shown in FIG. 4. The computer 146 collects, processes and stores the x-ray data. Detector 120 triggers ejector 128 and detector 118 triggers ejector 126 to fire on selected signals. The computer 146 measures the size distribution and amount of the material ejected into bin 130 using the difference in the signals from detectors 118 and 120. The computer 146 also detects the ejection efficiency with the ratio of ejected items and the number of the triggers to ejector 126. The computer 146 also uses the difference between detectors 121 and 120 to determine the sizes and number of ejected items by ejector 128. The computer 146 provides the size and number of detected particles in each bin 130, 132 and 134. This data allows the threshold settings of the detectors to be set for higher purity and lower product loss and it provides a measure of the sorting efficiency of the device 100.

In certain embodiments of the method, the detector threshold can be defined as a percent (for example 80%) of the signal voltage from the thickest regions of the sample of coal, without any inclusions of contaminants. The ejection threshold is then set as a percentage of pixel readings during the measurement cycle that have signals less than the detector threshold. The number of pixel signals with levels less than the threshold sets the minimum size of the ejected contaminate. A detector with 25 pixels/cm can detect 0.4 mm objects. Ejecting on a single low pixel reading could reduce contaminates to 100 ppm, but the product loss makes this impurity level impractical for coal. While ejection on a pixel may be useful for extracting gold from base rock, a more typical requirement for coal could be 250 pixels with low signals out of the typical 625 pixel signals per square cm of the sample.

In certain embodiments, the use of dual energy detectors permits determination of relative composition independent of coal thickness. In certain embodiments of the present invention, a complex pattern of matching size measurements of the coal sample is not needed, although it is preferred that the pieces of the sample have sizes less than the average bed depth of the coal sample. Stated another way, the methods disclosed herein operate to identify materials by differences in x-ray absorption and reliably provide signals to rapid ejection mechanisms.

With regard to determining an ejection threshold, applicants note that ejection is just one of several appropriate methods of physically separating pieces of the sample. In certain embodiments of the present invention, separation may occur by use of an array of air ejectors, as further described herein. In still other embodiments of the present invention, separation may occur by pushing, moving, or otherwise, thrusting a piece of sample which has reached an ejection threshold so that it is physically separated from a piece of sample which has not reached the ejection threshold. Such pushing or moving may occur by use of fast acting pistons, mechanical levers, or flippers. One of ordinary skill in the art is familiar with various arms, hydraulics, or the like which may be used to physically move a piece of sample which has reached the ejection threshold.

The present invention, as described herein, has recordable devices, such as microprocessors, controllers, computers, or the like, in order to allow the machines to make determinations and perform functions. One of ordinary skill in the art is familiar with adjusting, manipulating, or programming such devices in order to achieve the methods set forth herein. By way of example, the DXRT model commercially available from National Recovery Technologies, LLC of Nashville, Tenn., is programmable such that ejection thresholds may be set. In this example, the DXRT machine calculates position and timing information for arrival of the piece of sample at the air ejection array needed to accurately energize downstream ejector mechanisms in the air ejection array and issues the necessary commands at the right time to energize the appropriate ejectors to eject the piece of sample having a contaminant from the flow of other pieces of sample which do not have a contaminant. Accordingly, pieces of sample having sufficiently high percent transmissions are not ejected by the air ejection array. In alternate embodiments, the machine may be set such that the opposite is true. That is, sample containing no contaminants are ejected and pieces of sample containing contaminants are not ejected. Those of ordinary skill in the art recognize that such alterations to the methods disclosed herein may be performed.

One of ordinary skill in the art is familiar with the manner of operationally connecting components in detection systems as disclosed herein. All such wires, cables, and the like, needed for such operational connectivity are well known in the art and generally commercially available. Regarding each component of the present invention disclosed herein, operational connectivity includes any connections necessary for power, data or information transfer, or the like, for the operation of the specific device. One of ordinary skill in the art is familiar with such types of connections. Note that U.S. Pat. No. 6,610,981 issued to Sommer, Jr. on Aug. 26, 2003 is hereby incorporated by reference in its entirety.

Use of Infrared 3D Imaging with a Coal Sorter

The present invention includes an embodiment in which infrared 3D imaging enhances the efficiency of the coal sorter. By way of introduction, adding infrared 3D imaging to electromagnetic radiation material separation can greatly improve the separation efficiency and the throughput of the separation process. An embodiment of the present invention includes an infrared 3D imager 156 to track the position of each discrete piece of material being separated from the time it is identified using an electromagnetic radiation source 102 and detector 118 to the time it has arrived on the correct chute or conveyor. By including the 3D imager 156 with the coal sorter disclosed herein, the invention can verify correct separation of pieces, which depend upon the pieces maintaining predictable vectors of motion. Such invention can also measure the thickness of every piece being separated. This allows accurate separation decisions on a wide range of materials using measurements of single-energy x-rays, materials which before would have required the more costly and complicated measurement of x-rays of multiple energies.

Figure 8:
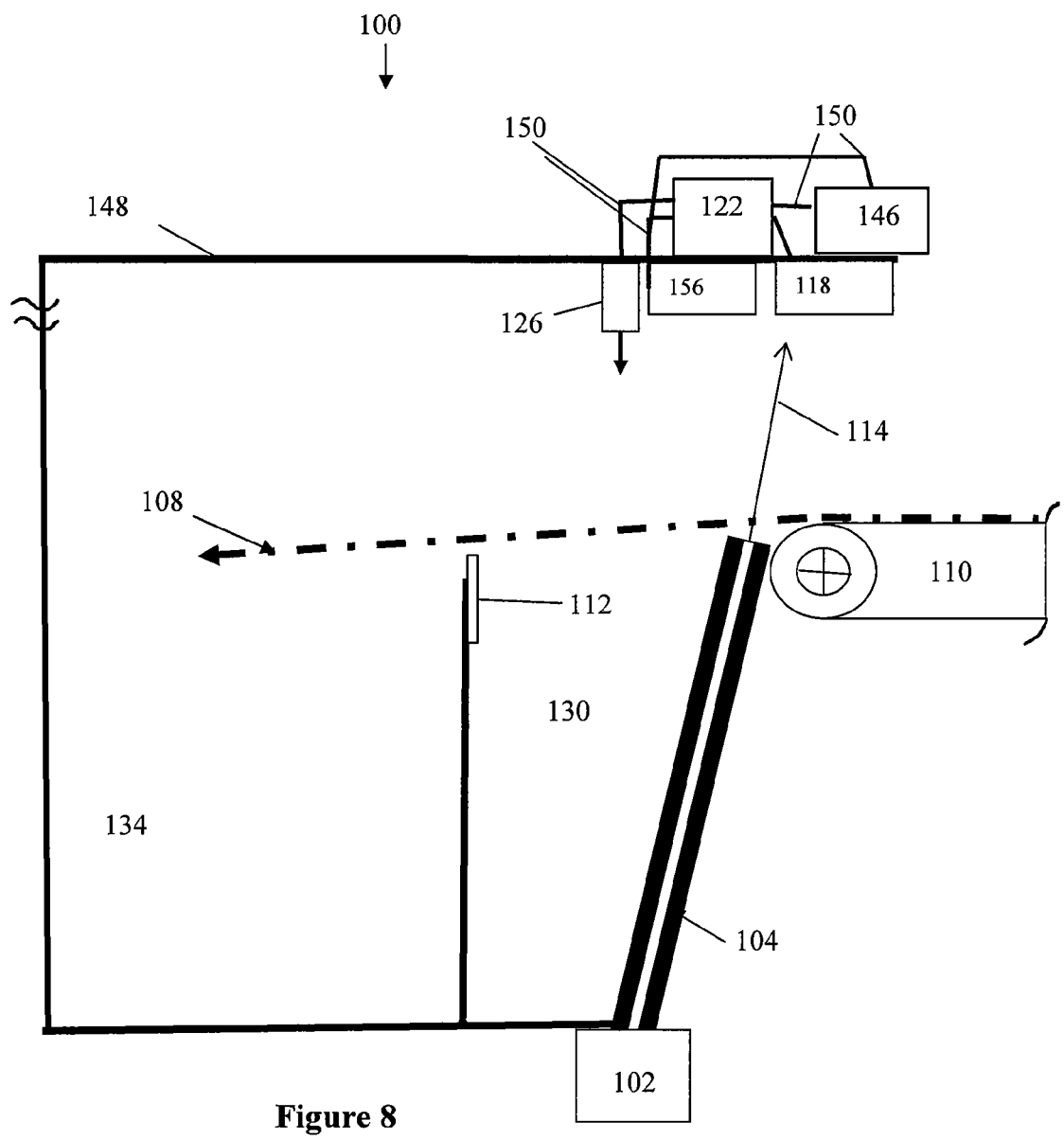
FIG. 8 shows a schematic diagram of a side view of an embodiment of a device for practicing the methods disclosed herein. Shown therein is a conveyor belt for transporting coal into a path between an x-ray source attached to a first collimator located beneath the sample stream, and a first x-ray detector located above the sample stream to receive the collimated x-rays. A 3D infrared imager tracks the position and motion of individual pieces of coal as they pass beneath the detector. Also shown is a computer and ejector system for separating the coal into the areas shown. The detector and the 3D infrared imager send signals to the computer which then sends signals to the ejector system. The purpose of this embodiment is to separate coal from rock with greater separation efficiency, higher speed, and/or lower cost.

Referring now to FIG. 8, there is shown an embodiment of the device 100 of the present invention including an infrared 3D imager 156. As shown therein, the infrared 3D imager 156 is positioned above the end of the conveyor 110 on which the sample stream 108 travels. The infrared 3D imager 156 is operationally connected to computer 146 by communication connections 150 so that information generated by the infrared 3D imager 156 is provided to the computer 146. That information includes geometry and motion information, such as position, velocity, direction of travel, acceleration, rotation, thickness, size, shape and orientation of pieces both before and after ejection. The computer 146 then controls the ejectors 126, as disclosed above, so that such additional information (i.e., shape, thickness, rotation, acceleration, velocity, direction of travel, etc.) is used to more efficiently separate the sample. The computer 146 is also receiving information and data from x-ray detector 118 through microprocessor 122 so that the x-ray detection information and 3D imager information are used in combination. In certain embodiments, the infrared 3D imager 156 is used with known electromagnetic radiation sorters. In other embodiments, the infrared 3D imager 156 is used with non-collimated x-ray beams.

Infrared 3D Imagers 156 are known in the art and readily commercially available. For example, an infrared 3D imager 156 may be purchased from Primesense in Tel Aviv, Israel. By way of background, an infrared 3D imager 156 illuminates the pieces of sample with continuously-projected, infrared structured light. By reading the infrared reflections with a CMOS sensor and calculating a dynamic, 3D representation of the material from the CMOS data using parallel computational logic, it may report the position, velocity, direction of travel, acceleration, rotation, size, shape, orientation and thickness of the pieces of material in the 3D representation or any combination of these parameters, as well as the results of calculations based on those parameters. Such information can improve the throughput and/or improve the separation efficiency and/or lower the operating cost of the separation process.

It is an unexpected benefit to have this further information. These position, shape, and size measurements mean the present invention equipment can operate at a higher capacity as the sample pieces can be in motion on vectors distinct from the motion vector of the conveyor. Further, the conveyor 110 density can be higher than normal as it is not as necessary to avoid collisions between the sample pieces. The size and shape measurements mean the power requirements of the separation process can be less as the intensity of the physical separation can be varied according to the size and shape of the sample piece. The thickness measurements mean the invention can report the thickness of the sample pieces at the point of identification to allow x-rays of a single energy to provide more information than is currently possible by simply measuring the x-ray absorption alone. In sum, all of these measurements can be made from before or at the point the sample pieces are examined by electromagnetic radiation to the time the sample pieces have definitely and finally passed through the sorter system and are in the collection bins, or on the chutes or conveyors for the rejected fraction or the collection bins, chutes or conveyors for the accepted fraction.

In certain embodiments of the present invention, when the infrared 3D imager 156 is tracking individual sample pieces, the following algorithm may be put in use:

1. At the point the sorter system makes the determination to keep or reject, with reject defined as the decision to employ the physical separation technology, e.g. air ejectors or other means, the shape, size and position of every sample piece designated for rejection is recorded.
2. The present invention tracks, in real time, sampling as often as is practical given the speed of the electronics of the day and given the speed of the sample material passing through the system, the position of the sample pieces designated for rejection as they moved towards the physical separation technology. The size, shape and previous position of the sample pieces uniquely identify each sample piece. In an alternate embodiment, the present invention may calculate the speed, direction of travel, acceleration or rotation of the sample pieces.
3. At the moment a sample piece designated for rejection arrives at the physical separation technology, the present invention triggers, or causes to be triggered, the physical separation technology at the optimum position given the position of the sample piece. In alternate embodiments, this decision could also be informed by the shape or size of the sample piece or the motion of the sample piece.
4. Because the size of each sample piece is mapped, the intensity of the physical separation according may vary according to the size, shape or orientation of the sample piece. For example, in the case of pneumatic separation, big sample pieces to be deflected would get more air.
5. The position of each sample piece marked for rejection continues to be tracked until it crosses a threshold marking it as definitely and finally having landed in a collection bin, or on the chute or conveyor carrying the rejected fraction, or another threshold marking it as definitely and finally being mis-classified and landing in a collection bin, or on the chute or conveyor carrying the accepted fraction. Optionally, data on the incidence of misclassification may be recorded and maintained. Also, optionally, such data may be used to vary, or cause to be varied, the speed of the conveyor feeding the sorter system or the intensity of the physical separation technology, or other appropriate parameters in an effort to minimize misclassification.
6. In the cases when the sample pieces marked for rejection missed the intended bins or chutes and bounced back into the mixed sample stream, the present invention maintains surveillance of the sample piece from steps 2-5 until the sample piece crosses a threshold marking it as definitely and finally out of the surveillance.

In other embodiments of the present invention, such as in the case of estimating the thickness of the individual sample pieces at the point of identification to allow x-rays of a single energy to provide more information, the following algorithm is of use:

1. Prior to operation, the infrared 3D imager 156 is calibrated with objects of known thickness at the point of x-ray identification. This calibration informs the infrared 3D imager 156 with the data required to report an accurate measurement of the object's thickness.
2. At the point the present invention makes the identification with single-energy x-rays, the infrared 3D imager 156 reports the thickness of the object at the point on the object through which the x-rays pass. This thickness datum combined with the datum of the x-ray absorption from the x-ray detector is used to make, or cause to be make, the decision to accept or reject the sample piece.
3. Optionally, as the sample pieces move towards the physical separation technology, the infrared 3D imager 156 re-samples the thickness estimate and revisits the decision to accept or reject. This step corrects for inaccuracy caused by an estimate of thickness from a single angle. In this case, all objects would be tracked through the infrared 3D imager 156, or at least all about which there had been some accept/reject ambiguity, and not just those marked for rejection.

The two algorithms are not exclusive. Both can and likely would be simultaneously used in many embodiments of the present invention. A person of ordinary skill in the art would, with software based on the above algorithms, be enabled to make an embodiment of this invention with a 30 Hz sampling rate using Microsoft's Kinect Controller for Xbox, which is readily commercially available. As known to one of ordinary skill in the art, an embodiment of the present invention with higher sampling rates and a higher-resolution pattern of structured infrared light could be made with software based on the above algorithms and Primesense's PS1080 system on a chip, their PrimeSensor Reference Design and their NITE middleware software, all of which are readily commercially available.

EXAMPLES

Example 1

Multi-fractional Sorting of ROM Coal with Multiple Collimated X-ray Beams

As shown in FIG. 1, ROM coal is placed on a fast conveyor 110 that gives the coal sufficient velocity to clear the splitter plates 112 and land in bin 134. The first x-ray detector 118 measures the absorption of the ROM coal stream. Again, the detectors may be located at the end of the conveyor 110 as shown in FIG. 1 or located under the belt of the conveyor 110 (not shown). The absorption signals are sent from the first detector 118 to the first microprocessor 122 which selects dense rocks with sizes greater than 0.75 inch and signals first sized ejector 126 to remove the selected rock from the ROM coal stream. The first sized ejector 126 has sufficient force to deflect heavy rocks into bin 130. The forceful ejection will also eject any coal adjacent to the heavy rock and screen 136 has 0.5 inch openings 140 that allow smaller pieces of rock and coal to pass into bin 142. The rock and coal in bin 142 can be returned to conveyor 110. The remaining small rocks and coal pass by the second detector 120 which measures absorption of the x-ray beam 116 by the sample. The second detector 120 is operationally connected to the second microprocessor 124, which may be set to select rock over 0.4 inch and signal the second sized ejector 128 to deflect such rock it into bin 132. The deflection of small sized rock does not require the force needed to deflect the more massive large rock and the use of smaller more numerous ejectors limit the amount of coal inadvertently ejected with the smaller rock. The smaller rock deflected into bin 132 falls on screen 138 which has 0.25 inch openings 140 that allow passage of the smaller sized items into bin 144, where such smaller items can be mixed with the coal product in bin 134. Obviously, sample that is not deflected has the velocity and projection to land in bin 134. While the preferred embodiment uses multiple x-ray beams from the same x-ray tube 102, in alternate embodiments, multiple x-ray beams can also be obtained by the use of two or more x-ray tubes 102.

Example 2

Multi-fractional Sorting of ROM Coal with a Single Collimated X-ray Beam

As shown in FIG. 6, the present invention combines certain features of the previously described embodiments herein to take advantage of the ability of a fine pitch x-ray detector to simultaneously measure absorption of x-rays passing through both large rocks and small rocks. That is, a single first collimator 104 provides an x-ray fan 114 to the first x-ray detector 118. The first x-ray detector 118 provides signals to the microprocessor 122 (not shown, but at same location as the detector 118). Importantly, the first sized ejectors 126 and the second sized ejectors 128 are not combined and remain positioned as shown with one downstream from the other. The x-ray fan 114 passes through the mineral or coal stream 108 and is detected and measured by detector 118. The measurements are processed by microprocessor 122 which runs an algorithm (not shown) that analyzes the measurements and distinguishes large rocks from smaller rocks while distinguishing both from the surrounding coal bed. Microprocessor 122 then signals ejectors 126 or 128 as appropriate to eject smaller rocks into bins 132 and larger rocks into bin 130. In effect this embodiment utilizes a single x-ray beam analysis system connected with a dual ejection system.

Example 3

Multi-fractional Sorting with a Measurement of Size and Number of Detected Objects in Product and Reject Bins FIG. 4 shows a device 100 with three x-ray beams 114, 116 and 117 from the same x-ray tube 102 that sorts large and small sized impurities into separate collection bins and uses the data from the three x-ray detectors 118, 120 and 121 to measure the number and size of detected objects in the product and reject bins. This embodiment provides the machine operator with running estimate of product loss and impurity. It also measures the ejection efficiency with the ratio of ejector triggers to items removed from the coal stream. The ejection efficiency data allows the machine operator to adjust the air amount to eject the impurity with minimal loss of coal.

Example 4

Inspection of ROM Coal without Sorting

As shown in FIG. 7, the present invention operates as an inspector without sorting. Specifically, the microprocessor 122 uses the absorption data from first x-ray detector 118 to determine the number and sizes of higher density rock in the coal sample and records this data in computer 146. Such information is useful as the price of coal is often determined by the rock content in the coal. The present invention makes it possible for power utilities to quickly sample larger quantities of coal.

All references, publications, and patents disclosed herein are expressly incorporated by reference.

Thus, it is seen that the methods and devices of the present invention readily achieve the ends and advantages mentioned as well as those inherent therein. While certain preferred embodiments of the invention have been illustrated and described for purposes of the present disclosure, numerous changes to the devices and methods may be made by those skilled in the art, which changes are encompassed within the scope and spirit of the present invention as defined by the following claims.

What is claimed is:

1. A multi-fractional coal sorting device, comprising:
   an x-ray tube, wherein the x-ray tube is in a fixed position;
   a first collimator attached to the x-ray tube;
   a second collimator attached to the x-ray tube;
   a first x-ray detector, wherein the first x-ray detector is in a fixed position to receive x-rays collimated by the first collimator;
   a second x-ray detector, wherein the second x-ray detector is in a fixed position to receive x-rays collimated by the second collimator;
   a first microprocessor operationally connected to the first x-ray detector;
   a first sized ejector operationally connected to the first microprocessor;
   a second microprocessor operationally connected to the second x-ray detector;
   a second sized ejector operationally connected to the second microprocessor;
   a first collection bin positioned to receive sample ejected by the first sized ejector;
   a second collection bin positioned to receive sample ejected by the second sized ejector;
   a first screen attached within the first collection bin, wherein the first screen defines a plurality of openings so that smaller sized objects may pass through the openings;
   a second screen attached within the second collection bin, wherein the second screen defines a plurality of openings so that smaller sized objects may pass through the openings.

2. The device of claim 1, wherein the first collection bin and the second collection bin are combined.

3. The device of claim 1, further comprising an infrared 3D imager positioned above a conveyor so that identifying characteristics of pieces of the sample on the conveyor are determined.

* * * * *